United States Patent

Qi et al.

(10) Patent No.: US 9,023,925 B2
(45) Date of Patent: *May 5, 2015

(54) PHOSPHOROUS-CONTAINING FLAME RETARDANTS FOR POLYURETHANE FOAMS

(75) Inventors: Yudong Qi, Zhangjiang (CN); Xiangyang Tai, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/001,903

(22) PCT Filed: Mar. 22, 2012

(86) PCT No.: PCT/CN2012/072802
§ 371 (c)(1),
(2), (4) Date: Nov. 7, 2013

(87) PCT Pub. No.: WO2012/126380
PCT Pub. Date: Sep. 27, 2012

(65) Prior Publication Data
US 2014/0058035 A1   Feb. 27, 2014

(30) Foreign Application Priority Data

Mar. 23, 2011  (WO) ............... PCT/CN2011/072072

(51) Int. Cl.
| | | |
|---|---|---|
| C08K 5/521 | (2006.01) | |
| C08K 5/527 | (2006.01) | |
| C08K 5/524 | (2006.01) | |
| C07F 9/6571 | (2006.01) | |
| C07F 9/6574 | (2006.01) | |
| C07D 407/12 | (2006.01) | |
| C08G 18/50 | (2006.01) | |
| C08G 18/66 | (2006.01) | |
| C07F 9/141 | (2006.01) | |
| C08G 18/38 | (2006.01) | |
| C08G 101/00 | (2006.01) | |

(52) U.S. Cl.
CPC ........... *C08K 5/524* (2013.01); *C07F 9/657154* (2013.01); *C07F 9/65742* (2013.01); *C07F 9/65746* (2013.01); *C07D 407/12* (2013.01); *C08G 18/5075* (2013.01); *C08G 18/6688* (2013.01); *C08G 2101/0008* (2013.01); *C08K 5/521* (2013.01); *C08K 5/527* (2013.01); *C07F 9/141* (2013.01); *C08G 18/3887* (2013.01)

(58) Field of Classification Search
USPC ................................. 524/140, 116
See application file for complete search history.

(56) References Cited

U.S. PATENT DOCUMENTS

| | | |
|---|---|---|
| 3,725,510 A | 4/1973 | Dever et al. |
| 3,758,646 A | 9/1973 | Boyer |
| 4,049,617 A | 9/1977 | Albright |
| 4,070,336 A | 1/1978 | Birum |
| 5,556,894 A | 9/1996 | Fishback et al. |
| 5,969,015 A | 10/1999 | Zinke et al. |
| 5,985,965 A | 11/1999 | Sicken et al. |
| 2006/0189729 A1 | 8/2006 | Bae et al. |
| 2010/0063169 A1 | 3/2010 | Stowell et al. |

FOREIGN PATENT DOCUMENTS

| | | |
|---|---|---|
| CN | 101624403 A | 1/2010 |
| EP | 0192154 A2 | 8/1986 |
| GB | 1108158 A | 4/1968 |
| GB | 1401985 A | 8/1975 |
| JP | 49023241 | 3/1974 |
| JP | 07-157652 A | 6/1995 |
| JP | 1995157652 | 6/1995 |
| WO | 0035999 A1 | 6/2000 |
| WO | 0044804 A2 | 8/2000 |
| WO | 2008/085926 A1 | 7/2008 |

OTHER PUBLICATIONS

PCT/CN2011/072072, International Search Report dated Dec. 22, 2011.
PCT/CN2011/072072, International Preliminary Report on Patentability dated Sep. 24, 2013.
PCT/ CN2011/072072, Written Opinion of the International Searching Authority dated Dec. 22, 2011.
PCT/CN2012/072802, International Search Report dated Jul. 5, 2012.

(Continued)

*Primary Examiner* — Peter Szekely

(57) ABSTRACT

Embodiments of the invention include a phosphorus containing flame retardant which may be the reaction product of a reaction mixture where the reaction mixture includes at least one active hydrogen-containing compound and at least one phosphorus containing compound. The at least one active hydrogen-containing compound is selected from the group of a first polyol having a hydroxyl functionality of at least 3, a polyamine having an amine functionality of at least 2, and an amino alcohol having a combined amine and hydroxyl functionality of at least 2. The at least one phosphorus containing compound has the general formula (1), (2) or combination thereof:

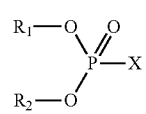

(1)

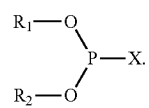

(2)

15 Claims, No Drawings

(56) References Cited

OTHER PUBLICATIONS

PCT/CN2012/072802, International Preliminary Report on Patentability dated Sep. 24, 2013.
PCT/CN2012/072802, Written Opinion of the International Searching Authority dated Jul. 5, 2012.
Supplementary European Search Report for EP12761119, Jul. 21, 2014, pp. 1-2.
Chellini, R. et al., Diethoxyphosphoryl as a protecting: activting group in the synthesis of polyazacyclophanes, Helvetica Chimaca Acta, 2000, pp. 793-800, vol. 83.
Bridger G.J., et al., Synthesis and structure-activity relationship of phenylenebi s(methylene)-1 inked bis-azamacrocycles that inhibit HIV-1 and HIV-2 replication by antagonism of the chemokine receptor CXCR, Journal of Medicinal chemistry, American Chemical Society, 1999, pp. 3971-3981, vol. 42.
Supplementary European Search Report for EP11861881, Sep. 23, 2014, pp. 1-4.
Grajkowski, et al., Journal of Organic Chemistry. 2007, pp. 805-815, vol. 72, No. 3.
Sakuma, T, et al., Tetrahedron Asymmetry, 2008, pp. 1593-1599, vol. 19, No. 13.
Grison, C., et al., Synthesis and antibacterial activity of novel enolphosphate derivatives, Bioorganic Chemistry, 2010, pp. 218-223, vol. 38.
Marosi, G., et al., A Study on the Selective Phosphorylation and Phosphinylation of Hydroxyphenols, Heteroatom Chemistry, 2002, pp. 126-130, vol. 13, No. 2.

PHOSPHOROUS-CONTAINING FLAME RETARDANTS FOR POLYURETHANE FOAMS

FIELD OF THE INVENTION

Embodiments of the invention relate to polyurethane foams, more specifically to flexible polyurethane foams.

BACKGROUND OF THE INVENTION

Polyurethanes are suitable for a large number of applications. To modify the polyurethanes behavior when exposed to fire, flame-retarding agents are usually added to these polyurethane materials. Phosphorous compounds, such as phosphates, phosphonates, and phosphites, are effective flame-retarding agents for polyurethane foam. In general phosphorus compounds may provide fire retardant activity through a combination of condensed phase reactions, gas phase radical quenching, polymer carbonization promotion, and/or char formation.

However, many phosphorus compounds are not soluble in the polyol formulations used to produce the polyurethanes. Therefore, there is a need for phosphorus compounds which are more compatible with the polyurethane formulations.

SUMMARY OF THE INVENTION

Embodiments of the invention include a phosphorus containing flame retardant which includes the reaction product of a first reaction mixture. The reaction mixture includes at least one active hydrogen-containing compound and at least one phosphorus containing compound. The at least one active hydrogen-containing compound is selected from a group including at least a first polyol having a hydroxyl functionality of at least 3, a polyamine having an amine functionality of at least 2, and/or an amino alcohol having a combined amine and hydroxyl functionality of at least 2. The at least one phosphorus containing compound has the general formula (1), (2) or combination thereof:

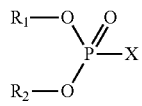

(1)

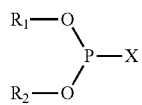

(2)

wherein X is a leaving group, $R_1$ and $R_2$ are, independently of one another, a $C_1$-$C_8$-alkyl, $C_1$-$C_4$-alkoxyethyl, $C_1$-$C_4$-alkyl-substituted $C_6$-$C_{10}$-aryl radical, alkyl substituted aryl, aryl substituted alkyl, nitro alkyl, hydroxyl alkyl, alkoxy alkyl, hydroxyl alkoxyalkyl, or $R_1$ and $R_2$ together form R in a six-membered ring, wherein the six membered ring has the general formula (3), (4) or combination thereof:

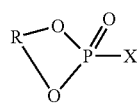

(3)

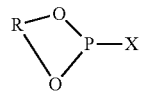

(4)

wherein R is a linear or branched divalent alkylene group containing from 3 to about 9 carbon atoms.

Embodiments also include a method of making a phosphorus containing flame retardant. The method includes reacting at least one active hydrogen-containing compound and at least one phosphorus containing compound. The at least one active hydrogen-containing compound is selected from a group including at least a first polyol having a hydroxyl functionality of at least 3, a polyamine having an amine functionality of at least 2, and/or an amino alcohol having a combined amine and hydroxyl functionality of at least 2. The at least one phosphorus containing compound has the general formula (1), (2) or combination thereof:

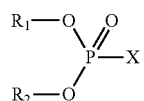

(1)

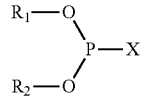

(2)

wherein X is a leaving group, $R_1$ and $R_2$ are, independently of one another, a $C_1$-$C_8$-alkyl, $C_1$-$C_4$-alkoxyethyl, $C_1$-$C_4$-alkyl-substituted $C_6$-$C_{10}$-aryl radical, alkyl substituted aryl, aryl substituted alkyl, nitro alkyl, hydroxyl alkyl, alkoxy alkyl, hydroxyl alkoxyalkyl, or $R_1$ and $R_2$ together form R in a six-membered ring, wherein the six membered ring has the general formula (3), (4) or combination thereof:

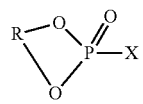

(3)

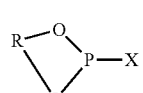

(4)

wherein R is a linear or branched divalent alkylene group containing from 3 to about 9 carbon atoms.

DESCRIPTION OF EMBODIMENTS OF THE INVENTION

Embodiments of the invention include for phosphorus compounds which are compatible with polyurethane formulations and are effective flame-retardants. The flame-retardants may be incorporated into formulations used to make polyurethane products such as foams. The flame-retardants are reaction products of at least an active hydrogen-containing compound and a phosphorus containing compound. The active hydrogen-containing compound may be a polyol having a hydroxyl functionality of at least 3, a polyamine having an amine functionality of at least 2, and/or an amino alcohol having a combined amine and hydroxyl functionality of at least 2.

Polyols are well known in the art and include those described herein and any other commercially available polyol. The polyols generally have a nominal functionality ranging from 3 to 10 and an average hydroxyl number ranging from 20 to 1850 mg KOH/g. The polyols may have a number average molecular weight of 60 to 10,000 g/mol. Mixtures of one or more polyols may also be used.

Representative polyols include polyether polyols, polyester polyols, polyhydroxy-terminated acetal resins, polyalkylene carbonate-based polyols, and hydroxyl-terminated amines and polyamines. Examples of these and other suitable isocyanate-reactive materials are described more fully in for example U.S. Pat. No. 4,394,491.

Embodiments encompass polyether polyols prepared by adding an alkylene oxide, such as ethylene oxide, propylene oxide, butylene oxide, or a combination thereof, to an initiator having from 2 to 8 active hydrogen atoms. Catalysis for this polymerization can be either anionic or cationic, with catalysts such as KOH, CsOH, boron trifluoride, or a double cyanide complex (DMC) catalyst such as zinc hexacyanocobaltate.

The initiators for the production of the polyols may have 3 to 8 functional groups that will react with alkylene oxides. Examples of suitable initiator molecules are polyhydric, in particular trihydric to hexatahydric alcohols or dialkylene glycols, for example glycerol, trimethylolpropane, pentaerythritol, sorbitol, and sucrose or blends thereof.

Embodiments may encompass amine initiated polyols which are initiated with an alkyl amine as given by the formula below (I) or containing an alkyl amine as part of the polyol chain.

$$H_m A\text{-}(CH_2)_n\text{—}N(R)\text{—}(CH_2)_p\text{-}AH_m \qquad (I)$$

where n and p are independently integers from 2 to 6, A at each occurrence is independently oxygen or nitrogen, m is equal to 1 when A is oxygen and is 2 when A is nitrogen.

In one embodiment, the at least one polyol includes at least one of polyoxalkylene polyol having an equivalent weight about 50-2500 g/mol. Alternatively, the at least one polyol has a number average molecular weight of at least 60 g/mol. For example, the number average molecular weight may be between 60 g/mol and 10000 g/mol. All individual values and subranges from 60 to 10,000 g/mol are included herein and disclosed herein; for example, the a number average molecular weight can be from a lower limit of 60, 103, 149, 250, 300, 500, 750, 1000, 2000, 2200, 2400, 2600, 3000, 4000, 5000, or 6000 g/mol, to an upper limit of 500, 750, 1000, 2000, 2200, 2400, 2600, 3000, 4000, 5000, 6000, 7000, 8000, 9000, or 10000 g/mol.

Such polyols may have a combined nominal functionality of about 3-10. All individual values and subranges from 3 to 10 are included herein and disclosed herein; for example, the a combined nominal functionality can be from a lower limit of 3, 4, 5, 6, 7, 8, or 9, to an upper limit of 4, 5, 6, 7, 8, 9, or 10.

The polyoxalkylene may include polyoxyethylene, polyoxypropylene, or a combination of both. In some embodiments, the polyols may be initiated with glycerol, sucrose, sorbitol, novolac or a combination of at least two of them. In some embodiments, the polyols may be polyoxyethylene capped and have a polyoxyethylene percentage of about 5-70%. Examples include SPECFLEX NC630, SPECFLEX NC 632, VORALUX HF 505, VORANOL 280, VORANOL CP260, VORANOL CP450, VORANOL CP 6001, VORANOL IP585, VORANOL RA800, VORANOL RA640, VORANOL RH360, VORANOL RN411, VORANOL RN482, and VORANOL RN490, all available from The Dow Chemical Company. Embodiments include using a mixture of different embodiments of these polyols.

Embodiments encompass sorbitol initiated polyoxypropylene polyols with an equivalent weight of between about 100 and about 200, such as VORANOL RN482 available from The Dow Chemical Company Embodiments encompass polyoxyethylene polyoxypropylene polyols initiated with a blend of glycerol and sucrose and having an equivalent weight of between about 100 and about 300 and a polyoxyethylene percentage of between about 15% and about 40%, such as VORANOL 280 available from The Dow Chemical Company.

Representative polyester polyols include those obtained from polycarboxylic acids and polyhydric alcohols. Examples of suitable polycarboxylic acids include oxalic acid, malonic acid, succinic acid, glutaric acid, adipic acid, pimelic acid, suberic acid, azelaic acid, sebacic acid, maleic acid, fumaric acid, glutaconic acid, α-hydromuconic acid, β-hydromuconic acid, α-butyl-α-ethyl-glutaric acid, α,β-diethylsuccinic acid, isophthalic acid, terephthalic acid, hemimellitic acid, and 1,4-cyclohexane-dicarboxylic acid. Any suitable polyhydric alcohol including both aliphatic and aromatic may be used such as ethylene glycol, 1,3-propylene glycol, 1,2-propylene glycol, 1,4-butylene glycol, 1,3-butylene glycol, 1,2-butylene glycol, 1,5-pentane diol, 1,4-pentane diol, 1,3-pentane diol, 1,6-hexane diol, 1,7-heptane diol, glycerol, 1,1,1,-trimethylolpropane, 1,1,1-trimethylolethane, hexane-1,2,6-triol, α-methyl glucoside, pentaerythritol, sorbitol, and sucrose or blends thereof. Also included are compounds derived from phenols such as 2,2-(4,4'-hydroxyphenyl)propane, commonly known as bisphenol A, bis(4,4'-hydroxyphenyl)sulfide, and bis-(4,4'-hydroxyphenyl) sulfone.

The polyamine having an amine functionality of at least 2 may include aromatic amines and aliphatic amines. Representative aromatic amines may include toluene diamine, 4,4'-methylene bis-2-chloroaniline, 2,2',3,3'-tetrachloro-4,4'-diaminophenyl methane, p,p'-methylenedianiline, p-phenylenediamine 4,4'-diaminodiphenyl, 2,4,6-tris(dimethylaminomethyl)phenol, 2,4-diethyl-6-methyl-1,3-benzenediamine, 4,4'-methylenbis(2,6-diethylbenzeneamine), dimethylthiotoluenediamine (DMTDA) such as E-300 from Albermarle Corporation (a mixture of 3,5-dimethylthio-2,6-toluenediamine and 3,5-dimethylthio-2,4-toluenediamine), diethyltoluenediamine (DETDA) such as E-100 Ethacure from Albermarle (a mixture of 3,5-diethyltoluene-2,4-diamine and 3,5-diethyltoluene-2,6-diamine). Representative aliphatic amines include glycol ethylene diamine, 1,4-butylenediamine, 1,6-hexamethylenediamine-1,2-diaminotheane, 1,3-diaminopropane, hexylmethylene diamine, methylene bis(aminocyclohexane), isophorone diamine, diethylenetriamine, 1,3- or 1,4-bis(aminomethyl)cyclohexane, and mixtures or blends thereof.

The amine may also be selected from the group consisting of amine terminated polyethers such as, for example, JEFFAMINE D-400 from Huntsman Chemical Company, 1,5-diamino-3-methyl-pentane, isophorone diamine, bis(aminomethyl)cyclohexane and isomers thereof, ethylene diamine, diethylene triamine, aminoethyl ethanolamine, triethylene tetraamine, triethylene pentaamine, ethanol amine, lysine in any of its stereoisomeric forms and salts thereof, hexane diamine, hydrazine and piperazine.

The polyamine having an amine functionality of at least 2 may have the structure as given in Formula (II) below:

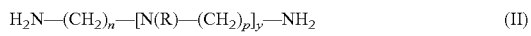

with n and p being independently integers from 2 to 6, R is hydrogen or a hydroxyalkyl having 2-6 carbons, and y being an integer from 0 to 25. In certain embodiments, the amine is diethylenetriamine (n=p=2, R=H, and y=1).

Representative amino alcohols having a combined amine and hydroxyl functionality of at least 2 include N-methylethanolamine, 4-aminocyclohexanol.

The amino alcohol having an amine functionality of at least 2 may have the structure as given in Formula (III) below:

with n and p being independently integers from 2 to 6, R is hydrogen or a hydroxyalkyl having 2-6 carbons, y being an integer from 0 to 25, A is independently nitrogen or oxygen, with at least one A being oxygen, and m being 2 when A is nitrogen and 1 when A is oxygen.

Suitable phosphorus containing compounds include one or more of the general formulas:

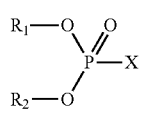

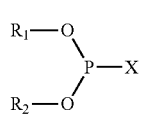

wherein X is a leaving group, such as for example Cl$^-$, Br$^-$, I$^-$, and sulfonate esters, such as para-toluenesulfonate ("tosylate", TsO$^-$); $R_1$ and $R_2$ are, independently of one another, a $C_1$-$C_8$-alkyl, $C_1$-$C_4$-alkoxyethyl, $C_1$-$C_4$-alkyl-substituted $C_6$-$C_{10}$-aryl radical, alkyl substituted aryl, aryl substituted alkyl, nitro alkyl, hydroxyl alkyl, alkoxy alkyl, hydroxyl alkoxyalkyl, or $R_1$ and $R_2$ together form R in an optionally $C_1$-$C_4$-alkyl-substituted, six-membered ring, such as in the formula as follows:

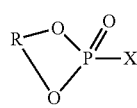

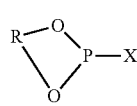

wherein R is a linear or branched divalent alkylene group containing from 3 to about 9 carbon atoms, such as propylene, 2-methylpropylene, neopentylene or 2-butyl-2-ethylpropylene. In one embodiment, the phosphorus containing compound is 2-Chloro-5,5-dimethyl-1,3,2-dioxaphosphinane (where R is neopentylene and X is Cl$^-$). Other suitable phosphorus containing compounds may include 2-chloro-5,5-dimethyl-1,3,2-dioxaphosphinane 2-oxide, diethyl phosphorochloridite, or diethyl phosphorochloridate.

The reaction of the at least one polyol and at the least one phosphorus containing compound may be performed in the presensce of an amine catalyst. The amine catalyst may be of the general formula N($R^1$)($R^2$)($R^3$), wherein each $R^1$, $R^2$, and $R^3$ is each independently the same or different linear, alkyl group containing from one to about 8 carbon atoms, branched alkyl group containing from 3 to about 8 carbon atoms, linear or branched alkenyl group containing up to about 8 carbon atoms, cyclic alkyl group containing from 5 to about 8 carbon atoms, or an aryl group containing from 6 to about 10 carbon atoms. In one non-limiting embodiment herein, each $R^1$, $R^2$, and $R^3$ group of the above general formula of the amine catalyst is independently the same or different and is selected from the group consisting of methyl, ethyl, propyl, butyl, isopropyl, isobutyl, sec-butyl, tert-butyl, isopentyl, neopentyl, isohexyl, isoheptyl, cyclohexyl and phenyl.

The reaction of the at least one polyol and at the least one phosphorus containing compound may be performed in the presence at least one solvent. For example, either or both of the at least one polyol and at the least one phosphorus containing compound may be dissolved in the solvent. The solvent may be any solvent which effectively solvates or suspends (with stirring) the phosphorus containing compound component. Effective solvation or suspension can vary greatly depending on the solvent and the amount of phosphorus containing compound employed in the method herein. Preferably, effective solvation/suspension can comprise sufficient solvent to effect solvation/suspension of from 50 weight percent of the phosphorus containing compound, based on the total weight of phosphorus containing compound, to an amount of solvent that is up to about 100 percent more solvent than is necessary for the complete dissolution/suspension of the total phosphorus containing compound being employed, said latter percent being based upon the total amount of solvent necessary to completely solvate/suspend the total amount of phosphorus containing compound being employed Suitable solvents may include toluene, xylene, cyclohexane, n-heptane, hexane, methyl acetate, ethyl acetate, chloromethane, dichloromethane, trichloromethane, hydroxyalkylphosphonate, xylene, tetrahydrofuran (THF), dimethyl formamide (DMF), petroleum ether, acetonitrile, methyl tert-butyl ether, acetone, methyl ethyl ketone, butyl acetate, and combinations thereof.

In some embodiments the reaction of the at least one polyol and at the least one phosphorus containing compound may be performed at reduced temperatures, such as between about −20° C. and about 40° C. In some embodiments the reaction temperature is maintained at between about −10° C. and about 30° C.

Embodiments encompass adding dissolved phosphorus containing compound to the at least one polyol which may optionally also be dissolved in a solvent. The at least amine catalyst may be dissolved with the at least one polyol before the phosphorus containing compound is added. Optionally, the at least one amine catalyst may be added to a dissolved mixture of the at least one polyol and at the least one phosphorus containing compound.

The reaction of the at least one polyol with the at least one phosphorus containing compound may proceed over time range of between about 10 minutes to about 10 hours. In some embodiments, the reaction time is about 2 hours.

The at least one polyol and at the least one phosphorus containing compound may be reacted at molar ratios such that the reaction has a capping index from 0.1 to 1. The capping index is the ratio of OH or amine functional groups per molecule of polyol that is reacted or capped with a phosphorus containing compound, as summarized in the following formula:

$$CI = Md/n \times Mp$$

where CI is the capping index, Md is the molar amounts of the at least one phosphorus containing compound, Mp is the molar amounts of the at least one polyol, amine or amino alcohol, and n is the nominal functionality of the at least one polyol, amine or amino alcohol.

A capping index of zero equates to no capped OH or amine, and a capping index of 1 equates to all the OH or amine groups being capped. With capping indexes of less than 1, the phosphorus containing flame retardant (FR) still have reactive OH or amine groups which may react with an isocyanate to form a urethane or urea linkage such that the phosphorus containing compound will be on a side chain of the polyurethane network through chemical linkages. The capping index may be any number from 0.05 to 1. All individual values and subranges between 0.05 and 1 are included herein and disclosed herein; for example, the capping index may be from a lower limit of 0.05, 0.1, 0.15, 0.2, 0.25, 0.3, 0.35, 0.4, 0.45, 0.5, 0.6, 0.67, 0.7, 0.75, 0.8, 0.85, or 0.9 to an upper limit of 0.25, 0.3, 0.35, 0.4, 0.45, 0.5, 0.6, 0.67, 0.7, 0.75, 0.8, 0.85, 0.9, 0.95, or 1.

The phosphorus of the flame retardant compounds made using the phosphorus containing compounds of formulas 2 and 4 may optionally be oxidized using suitable oxidizing agents such as manganate, permanganates, and peroxides, such as hydrogen peroxide.

The phosphorus containing flame retardant may be included in at least one polyol blend which is reacted with the isocyanate. The at least one polyol blend includes materials having at least one group containing an active hydrogen atom capable of undergoing reaction with an isocyanate. Suitable polyols are well known in the art and include those described above and any other commercially available polyol. Mixtures of one or more polyols and/or one or more polymer polyols may also be used to produce polyurethane products according to embodiments of the present invention.

The polyols may for example be poly(propylene oxide) homopolymers, random copolymers of propylene oxide and ethylene oxide in which the poly(ethylene oxide) content is, for example, from about 1 to about 30% by weight, ethylene oxide-capped poly(propylene oxide) polymers and ethylene oxide-capped random copolymers of propylene oxide and ethylene oxide. For slabstock foam applications, such polyethers preferably contain 2-5, especially 2-4, and preferably from 2-3, mainly secondary hydroxyl groups per molecule and have an equivalent weight per hydroxyl group of from about 400 to about 3000, especially from about 800 to about 1750. For high resilience slabstock and molded foam applications, such polyethers preferably contain 2-6, especially 2-4, mainly primary hydroxyl groups per molecule and have an equivalent weight per hydroxyl group of from about 1000 to about 3000, especially from about 1200 to about 2000. When blends of polyols are used, the nominal average functionality (number of hydroxyl groups per molecule) will be preferably in the ranges specified above. For viscoelastic foams shorter chain polyols with hydroxyl numbers above 150 are also used. For the production of semi-rigid foams, it is preferred to use a trifunctional polyol with a hydroxyl number of 30 to 80.

The polyether polyols may contain low terminal unsaturation (for example, less that 0.02 meq/g or less than 0.01 meq/g), such as those made using a DMC catalysts. Polyester polyols typically contain about 2 hydroxyl groups per molecule and have an equivalent weight per hydroxyl group of about 400-1500.

The polyols may be polymer polyols. In a polymer polyol, polymer particles are dispersed in the conventional petroleum-based polyol. Such particles are widely known in the art an include styrene-acrylonitrile (SAN), acrylonitrile (ACN), polystyrene (PS), methacrylonitrile (MAN), polyurea (PHD), or methyl methacrylate (MMA) particles. In one embodiment the polymer particles are SAN particles.

In addition to the above described polyols, the polyol blend may also include other ingredients such as catalysts, silicone surfactants, preservatives, and antioxidants, The polyol blend may be used in the production of polyurethane products, such as polyurethane foams, elastomers, microcellular foams, adhesives, coatings, etc. For example, the polyol blend may be used in a formulation for the production of flexible or rigid polyurethane foam. For the production of a polyurethane foam the polyol blend may be combined with additional ingredients such as catalysts, crosslinkers, emulsifiers, silicone surfactants, preservatives, flame retardants, colorants, antioxidants, reinforcing agents, fillers, including recycled polyurethane foam in form of powder.

Any suitable urethane catalyst may be used, including tertiary amine compounds, amines with isocyanate reactive groups and organometallic compounds. Exemplary tertiary amine compounds include triethylenediamine, N-methylmorpholine, N,N-dimethylcyclohexylamine, pentamethyldiethylenetriamine, tetramethyl-iethylenediamine, bis(dimethylaminoethyl)ether, 1-methyl-4-dimethylaminoethylpiperazine, 3-methoxy-N-dimethylpropylamine, N-ethylmorpholine, dimethylethanolamine, N-cocomorpholine, N,N-dimethyl-N',N'-dimethyl isopropylpropylenediamine, N,N-diethyl-3-diethylamino-propylamine and dimethylbenzylamine. Exemplary organometallic catalysts include organomercury, organolead, organoferric and organotin catalysts, with organotin catalysts being preferred among these. Suitable tin catalysts include stannous chloride, tin salts of carboxylic acids such as dibutyltin di-laurate. A catalyst for the trimerization of isocyanates, resulting in a isocyanurate, such as an alkali metal alkoxide may also optionally be employed herein. The amount of amine catalysts can vary from 0 to about 5 percent in the formulation or organometallic catalysts from about 0.001 to about 1 percent in the formulation can be used.

One or more crosslinkers may be provided, in addition to the polyols described above. This is particularly the case when making high resilience slabstock or molded foam. If used, suitable amounts of crosslinkers are from about 0.1 to about 10 parts by weight, such as from about 0.5 to about 3 parts by weight, per 100 parts by weight of polyols.

The crosslinkers may have three or more isocyanate-reactive groups per molecule and an equivalent weight per isocyanate-reactive group of less than 400. The crosslinkers preferably may include from 3-8, especially from 3-4 hydroxyl, primary amine or secondary amine groups per molecule and have an equivalent weight of from 30 to about 200, especially from 50-125. Examples of suitable crosslinkers include diethanol amine, monoethanol amine, triethanol amine, mono- di- or tri(isopropanol) amine, glycerine, trimethylol propane, pentaerythritol, and sorbitol.

It is also possible to use one or more chain extenders in the foam formulation. The chain extender may have two isocyanate-reactive groups per molecule and an equivalent weight per isocyanate-reactive group of less than 400, especially from 31-125. The isocyanate reactive groups are preferably hydroxyl, primary aliphatic or aromatic amine or secondary aliphatic or aromatic amine groups. Representative chain extenders include amines ethylene glycol, diethylene glycol, 1,2-propylene glycol, dipropylene glycol, tripropylene glycol, ethylene diamine, phenylene diamine, bis(3-chloro-4-aminophenyl)methane and 2,4-diamino-3,5-diethyl toluene. If used, chain extenders are typically present in an amount from about 1 to about 50, especially about 3 to about 25 parts by weight per 100 parts by weight high equivalent weight polyol.

A polyether polyol may also be included in the formulation, i.e, as part of the at least one conventional petroleum-based polyol, to promote the formation of an open-celled or softened polyurethane foam. Such cell openers generally have a functionality of 2 to 12, preferably 3 to 8, and a molecular weight of at least 5,000 up to about 100,000. Such polyether polyols contains at least 50 weight percent oxyethylene units, and sufficient oxypropylene units to render it compatible with the components. The cell openers, when used, are generally present in an amount from 0.2 to 5, preferably from 0.2 to 3 parts by weight of the total polyol. Examples of commercially available cell openers are VORANOL Polyol CP 1421 and VORANOL Polyol 4053; VORANOL is a trademark of The Dow Chemical Company.

The formulations may then be reacted with, at least one isocyanate to form a polyurethane product. Isocyanates which may be used in the present invention include aliphatic, cycloaliphatic, arylaliphatic and aromatic isocyanates.

Examples of suitable aromatic isocyanates include the 4,4'-, 2,4' and 2,2'-isomers of diphenylmethane diisocyante (MDI), blends thereof and polymeric and monomeric MDI blends, toluene-2,4- and 2,6-diisocyanates (TDI), m- and p-phenylenediisocyanate, chlorophenylene-2,4-diisocyanate, diphenylene-4,4'-diisocyanate, 4,4'-diisocyanate-3,3'-dimethyldiphenyl, 3-methyldiphenyl-methane-4,4'-diisocyanate and diphenyletherdiisocyanate and 2,4,6-triisocyanatotoluene and 2,4,4'-triisocyanatodiphenylether.

Mixtures of isocyanates may be used, such as the commercially available mixtures of 2,4- and 2,6-isomers of toluene diisocyantes. A crude polyisocyanate may also be used in the practice of this invention, such as crude toluene diisocyanate obtained by the phosgenation of a mixture of toluene diamine or the crude diphenylmethane diisocyanate obtained by the phosgenation of crude methylene diphenylamine. TDI/MDI blends may also be used.

Examples of aliphatic polyisocyanates include ethylene diisocyanate, 1,6-hexamethylene diisocyanate, isophorone diisocyanate, cyclohexane 1,4-diisocyanate, 4,4'-dicyclohexylmethane diisocyanate, 1,3-bis(isocyanatomethyl)cyclohexane, 1,4-bis(isocyanatomethyl)cyclohexane, saturated analogues of the above mentioned aromatic isocyanates, and mixtures thereof.

The at least one isocyanate is added to the blend for an isocyanate index of between about 30 and about 150, preferably between about 50 and about 120, more preferably between about 60 and about 110. The isocyanate index is the ratio of isocyanate-groups over isocyanate-reactive hydrogen atoms present in a formulation, given as a percentage. Thus, the isocyanate index expresses the percentage of isocyanate actually used in a formulation with respect to the amount of isocyanate theoretically required for reacting with the amount of isocyanate-reactive hydrogen used in a formulation.

For the production of flexible foams, the polyisocyanates may often be the toluene-2,4- and 2,6-diisocyanates or MDI or combinations of TDI/MDI or prepolymers made therefrom.

Isocyanate tipped prepolymer may also be used in the polyurethane formulation. Such prepolymers are obtained by the reaction of an excess of polyol.

Processing for producing polyurethane products are well known in the art. In general components of the polyurethane-forming reaction mixture may be mixed together in any convenient manner, for example by using any of the mixing equipment described in the prior art for the purpose such as described in "Polyurethane Handbook", by G. Oertel, Hanser publisher.

In general, the polyurethane foam is prepared by mixing the polyisocyanate of and polyol composition in the presence of the blowing agent, catalyst(s) and other optional ingredients as desired under conditions such that the polyisocyanate and polyol blend react to form a polyurethane and/or polyurea polymer while the blowing agent generates a gas that expands the reacting mixture. The foam may be formed by the so-called prepolymer method, in which a stoichiometric excess of the polyisocyanate is first reacted with the high equivalent weight polyol(s) to form a prepolymer, which is in a second step reacted with a chain extender and/or water to form the desired foam. Frothing methods are also suitable. So-called one-shot methods may be preferred. In such one-shot methods, the polyisocyanate and all polyisocyanate-reactive are simultaneously brought together and caused to react. Three widely used one-shot methods which are suitable for use in this invention include slabstock foam processes, high resilience slabstock foam processes, and molded foam methods.

Slabstock foam is conveniently prepared by mixing the foam ingredients and dispensing them into a trough or other region where the reaction mixture reacts, rises freely against the atmosphere (sometimes under a film or other flexible covering) and cures. In common commercial scale slabstock foam production, the foam ingredients (or various mixtures thereof) are pumped independently to a mixing head where they are mixed and dispensed onto a conveyor that is lined with paper or plastic. Foaming and curing occurs on the conveyor to form a foam bun. The resulting foams are typically from about from about 10 kg/m$^3$ to 100 kg/m$^3$, especially from about 15 kg/m$^3$ to 90 kg/m$^3$, preferably from about 17 kg/m$^3$ to 80 kg/m$^3$ in density.

In one embodiment, a slabstock foam formulation may contain from about 1 to about 6, preferably about 1.5 to about 5 parts by weight water are used per 100 parts by weight high equivalent weight polyol at atmospheric pressure. At reduced pressure these levels are reduced.

In the production of rigid polyurethane foams, the blowing agent includes water, and mixtures of water with a hydrocarbon, or a fully or partially halogenated aliphatic hydrocarbon. The amount of water is may be in the range between about 2 and about 15 parts by weight, preferably between about 2 and about 10 parts by weight based on 100 parts of the polyol. The amount of hydrocarbon, the hydrochlorofluorocarbon, or the hydrofluorocarbon to be combined with the water is suitably selected depending on the desired density of the foam, and may be less than about 40 parts by weight, preferably less than about 30 parts by weight based on 100 parts by weight of the polyol. When water is present as an additional blowing agent, it is may be present in an amount between about 0.5 and 10, preferably between about 0.8 and about 6, preferably between about 1 and about 4, and preferably between about 1 and about 3 parts by total weight of the total polyol composition.

Molded foam can be made according to the invention by transferring the reactants (polyol composition including copolyester, polyisocyanate, blowing agent, and surfactant) to a closed mold where the foaming reaction takes place to produce a shaped foam. Either a so-called "cold-molding"

process, in which the mold is not preheated significantly above ambient temperatures, or a "hot-molding" process, in which the mold is heated to drive the cure, can be used. Cold-molding processes are preferred to produce high resilience molded foam. Densities for molded foams generally range from 30 to 80 kg/m$^3$.

The phosphorus containing flame retardant may be included in at the total polyol blend at concentrations of between about 0.1 wt % and 35 wt % of the total polyol blend. All individual values and subranges between 0.1 wt % and 35 wt % are included herein and disclosed herein; for example, the phosphorus containing flame retardant may be from a lower limit of 0.1, 0.5, 1, 2, 3, 4, 5, 6, 7, 8, 9, 10, 11, 12, 14, 15, 16, 17, 18, 19, 20, 22, 25, 26, 28, or 30 wt % of total polyol blend, to an upper limit of 1, 2, 3, 4, 5, 6, 7, 8, 9, 10, 11, 12, 14, 15, 16, 17, 18, 19, 20, 22, 25, 26, 28, 30, or 35 wt % of the total polyol blend.

When used as described herein, the products made using the embodiments of the phosphorus containing flame retardant may exhibit better flame retardant properties than products made using comparative flame retardants such as trichloropropylphosphate, while at the same time maintaining good values for various physical properties such as tensile strength, tensile elongation, and tear strength. For example, the products described herein affords better FR performance at a lower concentration compared to products made using the halogen-containing trichloropropylphosphate.

For example, the embodied products may pass flame tests as developed by the State Of California, Department of Consumer Affairs, Bureau of Home Furnishings and Thermal Insulation, Technical Bulletin 117 (Requirements, Test Procedure and Apparatus for Testing the Flame Retardance of Resilient Filling Materials Used in Upholstered Furniture) of March 2000, section A part 1 (Cal 117).

The embodied products may pass flame test as described according to German Din 4102 B$_2$ testing.

EXAMPLES

The following examples are provided to illustrate the embodiments of the invention, but are not intended to limit the scope thereof. All parts and percentages are by weight unless otherwise indicated.

The following materials were used:

| | |
|---|---|
| VORANOL* RN482 | A sorbitol initiated polyoxypropylene polyol with an equivalent weight of 117, an OH value of 480 mg KOH/g, and a nominal functionality of 6. Available from The Dow Chemical Company. |
| VORANOL* 280 | An about 200 equivalent weight polyoxyethylene polyoxypropylene polyol initiated with a blend of glycerol and sucrose, having nominal functionality of around 6.9, a polyoxyethylene percentage around 25.6%, and an OH value of 280 mg KOH/g. Available from The Dow Chemical Company. |
| VORANOL* 3010 | An about 994 equivalent weight polyoxyethylene polyoxypropylene capped polyoxypropylene polyol initiated with glycerol, having nominal functionality of 3, a polyoxyethylene percentage of around 8%, and an OH value of 56 mg KOH/g. Available from The Dow Chemical Company |
| VORANOL* CP 1421 | An about 1,675 equivalent weight polyoxyethylene/polyoxypropylene capped polyoxypropylene polyol initiated with glycerol, having nominal functionality of 3, a polyoxyethylene percentage around 78%, and a hydroxyl number of about 32 mg KOH/g. Available from The Dow Chemical Company. |
| VORANOL* IP585 | An aromatic resin-initiated oxypropylene-oxyethylene polyol with hydroxyl number of 195 and average functionality of 3.3. Available from The Dow Chemical Company. |
| VORALUX* HF505HA | An about 1902 equivalent weight polyoxyethylene capped polyoxypropylene polyol initiated with sorbitol, having nominal functionality of 6, a polyoxyethylene percentage around 16%, and a hydroxyl number of about 29.5 mg KOH/g. Available from The Dow Chemical Company. |
| STEPANPOL PS-3152 | A diethylene glycol-phthalic anhydride based polyester polyol having OH value 300-330 mg KOH/g, functionality 2, available from Stepan Company. |
| MEG | Mono ethylene glycol, from SCRC |
| 2-Chloro-5,5-dimethyl-1,3,2-dioxaphosphinane | Available from Sigma Aldrich. |
| 2-Chloro-5,5-dimethyl-1,3,2-dioxaphosphorinane 2-oxide | Available from Sigma Aldrich |
| SAYTEX RB 79 | A brominated 2 functionality polyol available from Albemarle Corporation. |
| Triethylamine | Available from Sigma Aldrich. |
| Diethylenetriamine | Available from SCRC |
| TCPP | Trichloropropylphosphate, flame retardant from Zhangjiagang Changyu Chemical Co., Ltd. |
| H2O | Deionized water from Dow Chemical Company. |
| DEOA | N,N-Diethanolamine, OH value 1602, from Changzhou Jushun Chemical Company. |
| TEGOSTAB B 1048 | A silicone surfactant, commercially available from Evonik Industries. |
| TEGOSTAB B 8681 | A silicone surfactant, commercially available from Evonik Industries. |
| NIAX L 620 | A silicone surfactant available from Momentive Performance Materials. |
| DABCO 33-LV | A 33% solution of triethylenediamine in propylene glycol available from Air Products & Chemicals Inc. |

| | |
|---|---|
| NIAX A-1 | A 70% bis(2dimethyl aminoethyl)ether and 30% dipropylene glycol catalyst available from Momentive Performance Materials. |
| DABCO T-9 | A stannous octoate catalyst available from Air Products & Chemicals Inc. |
| HCFC-141b | 1,1-Dichloro-1-fluoroethane, blowing agent. Available from from Zhejiang Sanmei |
| VORANATE* T-80 | A toluene diisocyanate (80% 2,4-toluene diisocyanate and 20% 2,6-toluene diisocyanate by weight) composition available from The Dow Chemical Company. |
| PAPI 27 | A polymeric MDI (polymethylene polyphenylisocyanate) that contains MDI, and has an average molecular weight of 340 and an NCO content of 31.4%. Available from The Dow Chemical Company. |

*PAPI, VORALUX, VORANATE and VORANOL are trademarks of The Dow Chemical Company.

Example 1

VORANOL RN482 (210 g, 0.3 mol), triethylamine (151.5 g, 1.5 mol) and dichloromethane (600 mL) were charged into a three necked flask equipped with a mechanical stirrer. 2-Chloro-5,5-dimethyl-1,3,2-dioxaphosphorinane (202.3 g, 1.2 mol) in dichloromethane (200 mL) was added dropwise into the flask maintained at a temperature range of −10° C. to 10° C. The reaction was kept at this temperature range for 2 hours, after which triethylamine-HCl salt byproduct was removed by filtration. Solvent of the filtrate was removed by rotary evaporator. The residue was washed with water first, then the water was removed. The obtained product was dissolved in dichloromethane (600 mL) followed by water washing. The water layer was removed and solvent layer was further dried with anhydrous MgSO$_4$ overnight. The MgSO$_4$ was filtered and the dichloromethane solvent was removed to obtain FR Polyol A having on average two OH groups and four phosphite-containing groups per molecule as confirmed by proton and phosphorus NMR.

Polyurethane foams were prepared through hand-mixed trials in a plastic cup. For Example 1, FR Polyol A was blended with VORALUX HF505HA, VORANOL CP 1421, and DEOA (amounts given in Table 1), followed by 1 minute of mixing at 3000 rpm. Then, the other additives (TEGOSTAB B-8681, Water, DABCO T-9 and DABCO 33LV and NIAX A1 in a 3:1 ratio) were added, followed by mixing for one minute at 3000 rpm. Finally, VORANATE T-80 was added under high speed blending (about 3000-4000 rpm) for about 6 seconds. The obtained composition was poured into an open box for foaming. Comparative Examples 1-3 were prepared in a similar way, but with TCPP (Comparative Examples 2 and 3) or no flame retardant (Comparative Example 1) instead of FR Polyol A.

The foams were tested according to the State Of California, Department of Consumer Affairs, Bureau of Home Furnishings and Thermal Insulation, Technical Bulletin 117 (Requirements, Test Procedure and Apparatus for Testing the Flame Retardance of Resilient Filling Materials Used in Upholstered Furniture) of March 2000, section A part 1 (Cal 117). The flexible foams were cut into specimens (304.8 mm×76.2 mm×12.7 mm) using an electric saw. For each formulation, 10 specimens were tested (five before aging, 5 after aging). Specimens were exposed to a flame for 12 seconds and then After Flame Time (AFT) and Char Length were recorded.

The foams were cut into specimens for ASTM D3574-95-E tensile testing and ASTM D3574-95-F tear resistance testing. Tensile strength and elongation testing for flexible foam were carried out on an Instron 5565 with an upwards speed at 500 mm/min. For each formulation, 3 to 4 specimens were tested.

As shown in Table 1 for Cal 117 testing, addition of the FR-Polyol A into PU foam system increases FR performance dramatically (Example 1). Example 1 having 8 parts FR-polyol A has better FR performance than Comparative Example 2 with 15 parts TCPP and Comparative Example 3 with 18 parts TCPP. All comparative examples 1-3 failed the Cal 117 test. The results show that the FR-Polyol A affords better FR performance at lower loading compared to the halogen-containing TCPP. In addition, the addition of FR-Polyol A does not have a negative effect on the measured mechanical properties of the PU foam.

TABLE 1

| | Comparative example 1 | Comparative example 2 | Comparative example 3 | Example 1 |
|---|---|---|---|---|
| Components | | | | |
| VORALUX HF505HA | 100 | 100 | 100 | 100 |
| VORANOL CP 1421 | 2.5 | 2.5 | 2.5 | 2.5 |
| DEOA | 1.67 | 1.67 | 1.67 | 1.67 |
| TEGOSTAB B-8681 | 1.2 | 1.2 | 1.2 | 1.2 |
| DABCO 33LV, NIAX A1 (3:1) | 0.2 | 0.2 | 0.2 | 0.2 |
| Water | 3.3 | 3.8 | 4 | 3.4 |
| DABCO T-9 | 0.07 | 0.07 | 0.07 | 0.07 |
| TCPP | | 15 | 18 | |
| FR-polyol A | | | | 8 |
| VORANATE T-80 | 44.1 | 49.4 | 51.5 | 46.4 |
| Index | 108 | 108 | 108 | 108 |
| Properties | | | | |
| Density (Kg/m$^3$) | 31.15 | 30.6 | 31.55 | 31 |
| Tensile strength (KPa) | 46.0 | 45.2 | 49.0 | 46.7 |
| Tensile elongation (%) | 98.5 | 101.2 | 103.5 | 101 |
| Tear strength (N/m) | 132.9 | 139.6 | 153.1 | 162.3 |
| Cal 117 | >10 | 9 | 0 | 0 |
| AFT before aging (s) | >10 | >10 | 5 | 0 |
| | >10 | 0 | 7.5 | 0 |
| | >10 | 0 | 0 | 0 |
| | >10 | 0 | 2.5 | 0 |
| AFT after aging (s) | >10 | >10 | >10 | 0 |
| | >10 | >10 | 4 | 0 |
| | >10 | 0 | 1 | 0 |
| | >10 | 4 | 13 | 0 |
| | >10 | 7 | 3 | 0 |
| Char length before aging (mm) | Burn out | 170 | 60 | 45 |
| | Burn out | 195 | 155 | 65 |
| | Burn out | 54 | 150 | 55 |
| | Burn out | 78 | 20 | 60 |
| | Burn out | 66 | 50 | 55 |
| Char length after aging (mm) | Burn out | Burn out | 200 | 35 |
| | Burn out | Burn out | 105 | 40 |
| | Burn out | 72 | 100 | 40 |
| | Burn out | 90 | 190 | 50 |
| | Burn out | 100 | 90 | 55 |
| Pass or fail | fail | fail | fail | pass |

Example 2

VORANOL 280 (136.2 g, 0.1 mol), triethylamine (104.5 g, 1.035 mol) and dichloromethane (600 mL) were charged into a three necked flask equipped with a mechanical stirrer. 2-Chloro-5,5-dimethyl-1,3,2-dioxaphosphorinane (116.3 g, 0.69 mol) in dichloromethane (200 mL) was added dropwise into the flask maintained at a temperature range of −10° C. to 10° C. The reaction was kept at this temperature range for 2 hours, after which triethylamine-HCl salt byproduct was removed by filtration. Solvent of the filtrate was removed by rotary evaporator. The residue was washed with water first, then the water was removed. The obtained product was dissolved in dichloromethane (600 mL) followed by water washing. The water layer was removed and solvent layer was further dried with anhydrous $MgSO_4$ overnight. The MgSO4 was filtered and the dichloromethane solvent was removed to get an intermediate, a non-reactive phosphite, the precursor of FR B. The precursor was further oxidized using hydrogen peroxide (30% in water) added drop wise under stirring over 2 hours to obtain FR B. Proton and phosphorus NMR confirmed a full conversion of polyol OH groups.

Polyurethane foams were prepared through hand-mixed trials in a plastic cup. For Example 2, FR B was blended with VORANOL 3010, water, NIAX L 620, and DABCO T-9 and DABCO 33LV and NIAX A1 in a 3:1 ratio) (amounts given in Table 2), followed by mixing for one minute at 3000 rpm. Finally, VORANATE T-80 was added under high speed blending (about 3000-4000 rpm) for about 6 seconds. The obtained composition was poured into an open box for foaming. Comparative Examples 4 and 5 were prepared in a similar way, but with TCPP (Comparative Example 5) or no flame retardant (Comparative Example 4) instead of FR B.

As shown in Table 2 for Cal 117 testing, addition of the FR B into the polyurethane foam system increases FR performance dramatically (Example 2). Example 2, having 10 parts FR B, has better FR performance than the Comparative Example 5 with 30 parts TCPP. All comparative examples failed the Cal 117 FR testing. The results show that the FR B affords better FR performance at lower loading compared to the halogen-containing TCPP. In addition, the addition of FR B does not have a negative effect on the measured mechanical properties of the PU foam.

TABLE 2

| | Comparative example 4 | Comparative example 5 | Example 2 |
|---|---|---|---|
| Voranol 3010 | 100 | 100 | 100 |
| DABCO 33LV, NIAX A1 (3:1) | 0.36 | 0.36 | 0.27 |
| Water | 4 | 4 | 4 |
| NIAX L 620 | 1.2 | 1.2 | 1.2 |
| DABCO T-9 | 0.22 | 0.22 | 0.22 |
| TCPP | | 30 | |
| FR B | | | 10 |
| VORANATE T-80 | 51.1 | 51.1 | 51.1 |
| TDI Index | 95 | 95 | 95 |
| Properties | | | |
| Density (Kg/m³) | 27.5 | 33.2 | 26.8 |
| Rising time (sec) | 85 | 105 | 86 |
| Tensile strength (KPa) | 81.7 | 85.8 | 95.4 |
| Tensile elongation (%) | 130.1 | 155.5 | 164.2 |
| Tear strength (N/m) | 377.0 | 360.4 | 389.0 |
| Cal 117 | >10 | 0 | 7 |
| AFT before | >10 | 0 | 0 |
| aging (s) | >10 | 0 | 0 |
| | >10 | 0 | 2 |
| | >10 | 0 | 3 |
| AFT after | >10 | >10 | 3 |
| aging(s) | >10 | >10 | 1.5 |
| | >10 | >10 | 2 |
| | >10 | >10 | 1 |
| | >10 | 3 | 1 |
| Char length | Burn out | 35 | 125 |
| before aging | Burn out | 25 | 50 |
| (mm) | Burn out | 30 | 65 |
| | Burn out | 20 | 95 |
| | Burn out | 35 | 85 |
| Char length | Burn out | Burn out | 90 |
| after aging | Burn out | Burn out | 90 |
| (mm) | Burn out | Burn out | 85 |
| | Burn out | Burn out | 85 |
| | Burn out | 70 | 80 |
| Pass or fail | fail | fail | pass |

Examples 3-5

FR Polyol A* was made by further oxidizing FR Polyol A using hydrogen peroxide (30% in water) added drop wise under stirring over 2 hours.

The synthesis procedure of FR C was the same with FR polyol A*, except the mole radio of VORANOL RN482/2-chloro-5,5-dimethyl-1,3,2-dioxaphosphinane was 1/6. Proton and phosphorus NMR confirmed a full conversion of polyol OH groups.

PU rigid foam was prepared through hand-mixed trials in a plastic cup. Flame retardant (FR Polyol A, FR Polyol A*, FR C, or SAYTEX RB 79) was added into a polyol system, followed by 1 minute blending at 3000 rpm. Then other additives (catalysts, surfactants and foaming agents) were added, followed by another one-minute blending at 3000 rpm. Finally, isocyanate (component B) was added with high speed blending (about 3000-4000 rpm) for about 6 seconds. The obtained composition was poured into an open box for foaming Amounts in Table 3 are given in grams.

Preparation of specimens for German Din 4102 $B_2$ testing: the rigid foam was cut into specimens of 250 mm×90 mm×20 mm. The specimens were conditioned at 23±2° C. and 50±2% relative humidity for at least 24 h before FR testing. German Din 4102 $B_2$ Testing for rigid foam was conducted in a standard ISO 11925 chamber. For each sample, 3 pieces of specimen were tested. Each specimen was ignited 15 sec, with after flame time (AFT), maximum flame height, drip or not, was recorded.

Preparation of specimens for compressive strength testing: the rigid foam was cut into specimens 50 mm×50 mm×50 mm according to ASTM D695-89. The specimens were conditioned at 23±2° C. and 50±2% relative humidity for at least 24 h before testing. Compressive strength testing for rigid foam was conducted according to ASTM D695-89. Downward speed of the compressive plate was set at 10 mm/min, with the lowest displacement at 10% of the sample's thickness.

TABLE 3

|  | Comparative example 6 | Example 3 | Comparative example 7 | Example 4 | Example 5 |
|---|---|---|---|---|---|
| VORANOL IP585 | 6.6 | 6.6 | 6.6 | 6.6 | 6.6 |
| VORANOL RN482 | 36 | 36 | 36 | 36 | 36 |
| STEPANPOL PS-3152 | 14 | 14 | 14 | 14 | 14 |
| SAYTEX RB 79 | 25 |  | 25 |  |  |
| FR Polyol A |  | 25 |  |  |  |
| FR Polyol A* |  |  |  | 25 |  |
| FR C |  |  |  |  | 25 |
| DABCO 33LV | 0.5 | 0.5 | 0.6 | 0.6 | 0.6 |
| MEG | 4 | 4 | 4 | 4 | 4 |
| TEGOSTAB* B 1048 | 1.24 | 1.24 | 1.24 | 1.24 | 1.24 |
| HCFC-141b | 12 | 12 | 15 | 15 | 15 |
| $H_2O$ | 0.8 | 0.8 | 0.8 | 0.8 | 0.8 |
| ISO |  |  |  |  |  |
| Index | 1.15 | 1.15 | 1.15 | 1.15 | 1.15 |
| PMDI | 113.4 | 104.8 | 113.4 | 104.1 | 99.3 |
| Properties |  |  |  |  |  |
| Density/kg/$m^3$ | 43.2 | 42 | 35.1 | 33.6 | 32.8 |
| Din 4102 Flame height/mm | 230 | 170 | 250 | 140 | 150 |
|  | 230 | 180 | 260 | 160 | 160 |
|  | 250 | 170 | 265 | 150 | 150 |
| AFT/s | >20 | 0 | >20 | 0 | 0 |
|  | >20 | 1 | >20 | 0 | 0 |
|  | >20 | 0 | >20 | 0 | 1 |
| Compressive strength/Kpa | 272.3 | 272.1 |  |  |  |

Examples 6 and 7

VORANOL RN482 (210 g, 0.3 mol), triethylamine (151.5 g, 1.5 mol) and dichloroethane (600 mL) were charged into a three necked flask equipped with a mechanical stirrer. Diethyl phosphorochloridite (187.2 g, 1.2 mol) in dichloroethane (200 mL) was added dropwise into the flask maintained at a temperature range of −10° C. to 10° C. The reaction was kept at this temperature range for 1 hour, and then the reaction was heated to 15° C. to 25° C. and stirred for 1 more hour. The reaction mixture was washed with water. The water layer was removed and solvent layer was further dried with anhydrous $Na_2SO_4$ for 20 minutes and filtered. The filtrate was evaporated under reduced pressure, the majority of solvent was removed at 40° C. for about 1 hour, then the small quantity of solvent residue was removed under high vacuum at 25° C. for 3 hs to obtain FR Polyol D having on average two OH groups and four phosphite-containing groups per molecule as confirmed by proton and phosphorus NMR.

Diethylenetriamine (10.3 g, 0.1 mol), triethylamine (33.3 g 0.33 mol) and methylene dichloride (100 ml) were charged into a three necked flask equipped with a mechanical stirrer. 2-Chloro-5,5-dimethyl-1,3,2-dioxaphosphorinane 2-oxide (36.9 g, 0.3 mol) was portion-wise added into the flask at below 10° C. The reaction was kept at room temperature for about 16 hours. Then the reaction solution was washed by water 3 times. The organic layer was dried with anhydrous $Na_2SO_4$, the solvent was removed under reduced pressure and the final product (FR E) was produced at around 90% yield.

PU Foam was prepared through hand-mixed trials in a plastic cup. Flame retardant (FR Polyol D, FR E, or TCPP) was added into a polyol system, followed by 1 minute blending at 3000 rpm. Then other additives (such as catalysts, surfactants and foaming agents) were added, followed by another one-minute blending at 3000 rpm. Finally, isocyanate (VORANATE T-80) was added with high speed blending (about 3000-4000 rpm) for about 6 seconds. The obtained composition was poured into an open box for foaming.

The foams were tested according to the State Of California, Department of Consumer Affairs, Bureau of Home Furnishings and Thermal Insulation, Technical Bulletin 117 as described above. Tensile & Elongation and Tear Resistance testing were performed according to ASTM D3574-95-E tensile testing and ASTM D3574-95-F tear resistance testing.

Resilience testing was performed according to ASTM D3574-95-H by a ball rebound tester.

As shown in Table 4 for Cal117 FR testing, addition of the FR polyol D into the PU foam system increases FR performance dramatically (Example 6). The Example 6 comprising 10 parts FR polyol D has better FR performance than the comparative example 9 with 30 parts TCPP. Comparative examples 8 and 9 failed the Cal117 FR testing. The results show that the FR polyol D affords better FR performance at lower loading compared to the halogen-containing TCPP. In addition, the addition of FR polyol D has no adverse effect on mechanical properties of the PU foam.

It can also be seen that As the addition of the FR E into the PU foam system increases FR performance dramatically (Example 7). The example 7 comprising 5 parts FR E has better FR performance than the comparative example 11 with 15 parts TCPP. Comparative examples 10 and 11 failed the Cal117 FR testing. The results show that the FR E affords better FR performance at lower loading compared to the halogen-containing TCPP. In addition, the addition of FR-E has no adverse effect on mechanical properties of the PU foam.

TABLE 4

| | Comparative example 8 | Comparative example 9 | Example 6 | Comparative example 10 | Comparative example 11 | Example 7 |
|---|---|---|---|---|---|---|
| VORANOL 3010 | 100 | 100 | 100 | | | |
| VORALUX-HF505HA | | | | 100 | 100 | 100 |
| VORANOL CP1421 | | | | 2.5 | 2.5 | 2.5 |
| DABCO 33LV, NIAX A1 (3:1) | | 0.36 | 0.24 | 0.2 | 0.2 | 0.2 |
| DEOA | | | | 1.67 | 1.67 | 1.67 |
| TEGOSTAB B-8681 | | | | 1.2 | 1.2 | 1.2 |
| H2O | 4 | 4 | 3.8 | 3.3 | 3.8 | 3.8 |
| NIAX L 620 | 1.2 | 1.2 | 1.2 | | | |
| DABCO T9 | | 0.22 | 0.22 | 0.07 | 0.07 | 0.07 |
| FR polyol D | | | 10 | | | |
| FR E | | | | | | 5 |
| TCPP | | 30 | 0 | | 15 | |
| TDI Index | 95 | 95 | 95 | 108 | 108 | 108 |
| VORANATE T-80 | 51.1 | 51.1 | 51.4 | 44.1 | 49.4 | 50.2 |
| Properties | | | | | | |
| Density (Kg/m³) | 27.5 | 33.2 | 32.6 | 31.15 | 30.6 | 30.6 |
| Tensile strength (KPa) | 81.7 | 85.8 | 86.8 | 46 | 45.2 | 45.2 |
| Tensile elongation (%) | 130.1 | 155.5 | 131.4 | 98.5 | 101.2 | 101.2 |
| Tear strength (N/m) | 377 | 360.4 | 376 | 132.9 | 139.6 | 139.6 |
| Resilience (%) | 32 | 29 | 31 | | | |
| FR performance (Cal 117) | fail | fail | pass | fail | fail | pass |
| AFT before aging (sec) (Cal 117) | | 0 | 7 | >10 | 9 | 0 |
| | | 0 | 0 | >10 | 14 | 0 |
| | | 0 | 0 | >10 | 0 | 0 |
| | | 0 | 2 | >10 | 0 | 0 |
| | | 0 | 3 | >10 | 0 | 0 |
| AFT after aging (sec) (Cal 117) | | >10 | 3 | >10 | >20 | 0 |
| | | >10 | 1.5 | >10 | >20 | 0 |
| | | >10 | 2 | >10 | 0 | 0 |
| | | >10 | 1 | >10 | 4 | 0 |
| | | 3 | 1 | >10 | 7 | 0 |
| Char length before aging(mm) | | 35 | 125 | QBO | 170 | 50 |
| | | 25 | 50 | QBO | 195 | 40 |
| | | 30 | 65 | QBO | 54 | 45 |
| | | 20 | 95 | QBO | 78 | 35 |
| | | 35 | 85 | QBO | 66 | 40 |
| Char length after aging(mm) | | Burn out | 90 | QBO | Burn out | 45 |
| | | Burn out | 90 | QBO | Burn out | 50 |
| | | Burn out | 85 | QBO | 72 | 40 |
| | | Burn out | 85 | QBO | 90 | 40 |
| | | Burn out | 80 | QBO | 100 | 40 |

While the foregoing is directed to embodiments of the present invention, other and further embodiments of the invention may be devised without departing from the basic scope thereof, and the scope thereof is determined by the claims that follow.

The invention claimed is:

1. A phosphorus containing flame retardant comprising the reaction product of a reaction mixture, comprising:

(1) at least one active hydrogen-containing compound that is:

(a) a first polyol having a hydroxyl functionality of at least 5, (b) a polyamine having an amine functionality of 2 and the structure as given in Formula (II):

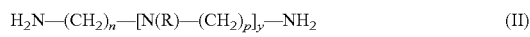

$H_2N-(CH_2)_n-[N(R)-(CH_2)_p]_y-NH_2$ (II)

wherein n and p are independently integers from 2 to 6, R is a hydroxyalkyl having 2-6 carbons, and y is 1;

(2) at least one phosphorus containing compound having the general formula (1), (2) or combination thereof:

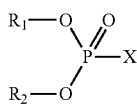

(1)

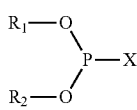

(2)

wherein X is a leaving group, $R_1$ and $R_2$ are, independently of one another, a $C_1$-$C_8$-alkyl, $C_1$-$C_4$-alkoxy-ethyl, $C_1$-$C_4$-alkyl-substituted $C_6$-$C_{10}$-aryl radical, alkyl substituted aryl, aryl substituted alkyl, nitro alkyl, hydroxyl alkyl, alkoxy alkyl, hydroxyl alkoxy-alkyl, or $R_1$ and $R_2$ together form R in a six-membered ring, wherein the six membered ring has the general formula (3), (4) or combination thereof:

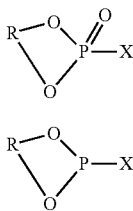

wherein R is a linear or branched divalent alkylene group containing from 3 to about 9 carbon atoms.

2. A method of making a phosphorus containing flame retardant, the method comprising:
reacting at least:
(1) at least one active hydrogen-containing compound that is:
(a) a first polyol having a hydroxyl functionality of at least 5,
(b) a polyamine having an amine functionality of 2 and the structure as given in Formula (II):

$$H_2N\text{---}(CH_2)_n\text{---}[N(R)\text{---}(CH_2)_p]_y NH_2 \quad \text{(II)}$$

wherein n and p are independently integers from 2 to 6, R is a hydroxyalkyl having 2-6 carbons, and y is 1;
(2) at least one phosphorus containing compound having the general formula (1), (2) or combination thereof:

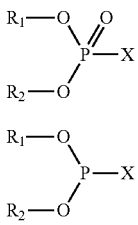

wherein X is a leaving group, $R_1$ and $R_2$ are, independently of one another, a $C_1$-$C_8$-alkyl, $C_1$-$C_4$-alkoxyethyl, $C_1$-$C_4$-alkyl-substituted $C_6$-$C_{10}$-aryl radical, alkyl substituted aryl, aryl substituted alkyl, nitro alkyl, hydroxyl alkyl, alkoxy alkyl, hydroxyl alkoxyalkyl, or $R_1$ and $R_2$ together form R in a six-membered ring, wherein the six membered ring has the general formula (3), (4) or combination thereof:

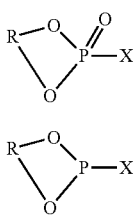

wherein R is a linear or branched divalent alkylene group containing from 3 to about 9 carbon atoms.

3. The phosphorus containing flame retardant of claim 1, wherein $R_1$ and $R_2$, independently of each other, are propylene, 2-methylpropylene, or neopentylene.

4. The phosphonate flame retardant of claim 1, wherein X is selected from the group consisting of Cl, Br, and I, and sulfonate.

5. The phosphorus containing flame retardant of claim 1, wherein the phosphorus containing compound is 2-Chloro-5,5-dimethyl-1,3,2-dioxaphosphinane, 2-chloro-5,5-dimethyl-1,3,2-dioxaphosphinane 2-oxide, diethyl phosphorochloridite, or diethyl phosphorochloridate.

6. The phosphorus containing flame retardant of claim 1, wherein the first polyol is included in the reaction mixture and the first polyol comprises at least one of polyoxalkylene polyol having an equivalent weight about 60-2500.

7. The phosphorus containing flame retardant of claim 6, wherein the at least one polyoxalkylene polyol is initiated with sucrose, sorbitol, or a combination thereof, and the polyoxalkylene comprises at least one of polyoxyethylene and polyoxypropylene.

8. The phosphorus containing flame retardant of claim 1, wherein the first polyol is included in the reaction mixture and the first polyol comprises a sorbitol initiated polyoxypropylene polyol with an equivalent weight of between about 100 and about 200.

9. The phosphorus containing flame retardant of claim 1, wherein the first polyol is included in the reaction mixture and the first polyol comprises a polyoxyethylene polyoxypropylene polyol initiated with a blend of glycerol and sucrose and having an equivalent weight of between about 100 and about 300 and a polyoxyethylene percentage of between about 15% and about 40%, based on the weight of the polyoxyethylene polyoxypropylene polyol.

10. The phosphorus containing flame retardant of claim 1, wherein the phosphorus containing flame retardant has a capping index such that the at least one first polyol has on average at least one phosphorus containing compound reacted with a polyol OH site.

11. The phosphorus containing flame retardant of claim 1, wherein the phosphorus containing flame retardant has a capping index such that the at least one first polyol has on average at least half of its polyol OH sites capped by the at least one phosphorus containing compound.

12. The phosphorus containing flame retardant of 1, wherein the phosphorus containing flame retardant has a capping index such that the at least one first polyol has on average substantially all of its polyol OH sites capped by the at least one phosphorus containing compound.

13. A polyurethane product comprising the reaction product of:
at least one isocyanate; and
a polyol blend that includes the phosphorous containing flame retardant as claimed in claim 1 and at least one second polyol.

14. The polyurethane product of claim 13 which passes Cal 117 testing or Din 4102 Testing.

15. The polyurethane product of claim 13, wherein the phosphorus containing flame retardant comprises between about 0.1 wt % and 35 wt % of the polyol blend.

* * * * *